(12) United States Patent
Nimmo et al.

(10) Patent No.: US 9,180,464 B2
(45) Date of Patent: Nov. 10, 2015

(54) SORTING APPARATUS FOR ARTHROPODS AND METHOD OF USE THEREOF

(71) Applicant: Oxitec Limited, Abingdon, Oxfordshire (GB)

(72) Inventors: Derric David Nimmo, Abingdon (GB); Luke Alphey, Abingdon (GB)

(73) Assignee: OXITEC LIMITED, Abingdon (GB)

( * ) Notice: Subject to any disclaimer, the term of this patent is extended or adjusted under 35 U.S.C. 154(b) by 0 days.

(21) Appl. No.: 14/491,870

(22) Filed: Sep. 19, 2014

(65) Prior Publication Data

US 2015/0008163 A1  Jan. 8, 2015

Related U.S. Application Data

(63) Continuation of application No. PCT/GB2013/050723, filed on Mar. 20, 2013.

(30) Foreign Application Priority Data

Mar. 20, 2012 (GB) .................................. 1204860.9

(51) Int. Cl.
| | |
|---|---|
| *B07B 1/12* | (2006.01) |
| *B03B 5/50* | (2006.01) |
| *A01K 67/033* | (2006.01) |
| *B07B 1/46* | (2006.01) |
| *B07B 13/04* | (2006.01) |

(52) U.S. Cl.
CPC ................. *B03B 5/50* (2013.01); *A01K 67/033* (2013.01); *B07B 1/12* (2013.01); *B07B 1/4636* (2013.01); *B07B 13/04* (2013.01)

(58) Field of Classification Search
CPC .......... B07B 1/12; B07B 1/16; B07B 1/4636; B07B 2230/01; B03B 5/50; A01K 67/033
USPC ...................... 209/17, 394, 668, 676
See application file for complete search history.

(56) References Cited

U.S. PATENT DOCUMENTS

| 742,158 | A | | 10/1903 | Burke | |
|---|---|---|---|---|---|
| 1,289,778 | A | * | 12/1918 | Houck | ........................... 209/394 |
| 3,204,605 | A | * | 9/1965 | Vroman | ........................ 209/676 |
| 3,833,119 | A | * | 9/1974 | Brown | ........................... 209/675 |
| 5,248,046 | A | * | 9/1993 | Rollason | ....................... 209/675 |
| 7,134,238 | B2 | * | 11/2006 | Forehand | ........................ 43/122 |
| 7,448,498 | B2 | * | 11/2008 | McRobert | ...................... 209/394 |

(Continued)

FOREIGN PATENT DOCUMENTS

GB  408 050  4/1934

OTHER PUBLICATIONS

Sharma et al., Bulletin of WHO, p. 429-432, 1974.*

(Continued)

*Primary Examiner* — Joseph C Rodriguez
(74) *Attorney, Agent, or Firm* — Morrison & Foerster LLP

(57) ABSTRACT

There is provided an apparatus for sorting arthropod larvae and pupae and in particular, although not necessarily, to sorting arthropod pupae on the basis of size, especially in mosquitoes. The apparatus can contain two parallel bars pivotally mounted in a frame such that the distance between the bars is adjustable. Insect larvae and pupae may be inserted into a chamber with one side formed by the grid of bars and inserted into water to separate the different forms.

17 Claims, 6 Drawing Sheets

(56) References Cited

U.S. PATENT DOCUMENTS 8,844,465 B2* 9/2014 Holland et al. ............... 119/6.5
2014/0332448 A1* 11/2014 Trivette et al. ............... 209/17

OTHER PUBLICATIONS

Ansari et al., "A device for separation of pupae from larvae of Aedes aegypti (Diptera: Culicidae)," J. Med. Entomol. (1977) 14(2):241-243.

Ansari et al., The development of procedures for mass rearing of Aedes aegypti (I). WHO/VBC/75.560:9P (1975) 9 pages.

Evans et al., "A simple separator for mosquito larvae and pupae," Mosq. News (1968) 28(4):649-650.

Fay et al., "A mechanical device for separating the developmental stages, sexes, and species of mosquitos," Mosq. News (1959) 19:144-147.

Fay et al., "Mass production of sterilized male Aedes aegypti," (1963) Mosq. News 23(3):210-214.

Focks, "An improved separator for the developmental stages, sexes, and species of mosquitos (Diptera: Culicidae)," J. Med. Entomol. (1980) 17:567-568.

Hazard, "Modification of the ice water method for harvesting Anopheles and Culex pupae," Mosq. News (1967) 27:115-116.

International Preliminary Report on Patentability for PCT/GB2013/050723, issued Sep. 23, 2014, 8 pages.

International Search Report for PCT/GB2013/050723, mailed Jul. 12, 2013, 5 pages.

Lin et al., "Tolerance of mosquito larvae and pupae to carbon dioxide anesthesia," Mosq. News (1976) 36:460-461.

McCray, "A mechanical device for the rapid sexing of Aedes aegypti pupae," J. Econ. Entomol. (1961) 54:819.

Ramakrishnan et al., "A simple technique for rapid separation of mosquito pupae by sudden chilling," (1963) Indian J. Malarlol. (1963) 17(2/3):119-121.

Weathersby, "Harvesting mosquito pupae with cold water," Mosq. News (1963) 23(3):249-251.

* cited by examiner

SORTING APPARATUS FOR ARTHROPODS AND METHOD OF USE THEREOF

CROSS-REFERENCE TO RELATED APPLICATIONS

This application is a continuation of International Application No. PCT/GB2013/050723 filed Mar. 20, 2013 which claims priority to Great Britain Application No. GB1204860.9 filed Mar. 20, 2012. The contents of these applications are incorporated herein by reference in their entirety.

TECHNICAL FIELD

The present invention relates to sorting apparatus for sorting arthropods, preferably insect, larvae and/or pupae and in particular, although not necessarily, to sorting pupae on the basis of size and thus also to sorting pupae on the basis of sex. The apparatus and method are particularly, although not necessarily, for use in sorting insect larvae and/or pupae in particular in mosquitoes.

BACKGROUND

The use of sterile insects to control an insect population, such as that of the mosquito, requires millions of insects to be reared, sterilised and released. In order to release insects on the scale required the process of rearing has to be as automated as possible in order to be cost effective.

For some insect types there is no need to sort the insects on the basis of sex before they are released. However, for other insects it is essential to remove the females, for example, because they transmit disease or damage crops. As in mosquitoes the females transmit disease the sorting process for mosquitoes should be optimised to reduce to the minimum level possible the number of female mosquitoes released whilst minimising any loss of male mosquitoes.

Due to the differing life cycles of male and female mosquitoes two main stages of sorting are generally required for a release program. First, larvae need to be sorted from the pupae and then male pupae must be sorted from the female pupae. This may be achieved on the basis of differing sizes of larvae and pupae, for instance if male pupae and female pupae are different sizes (i.e. on average (mean) at the same time period in development). For example, in *Ae. aegypti*, larvae are smaller, of a different shape and thinner than male pupae. Moreover, pupae tend to float whilst larvae are prone to sink. Male pupae are smaller than female pupae.

In mosquitoes there have been several large scale rearing programs which have attempted to automate the rearing and separation of mosquitoes in their different life stages. Examples of known devices and methods which have been developed to automate sorting mosquitoes will now be described with reference to FIGS. 1 to 3.

One example of a sorting machine which was first described in Focks, D. (1980). "An improved separator for the developmental stages, sexes, and species of mosquitoes (Diptera: Culicidae)." *J Med Entomol*, 17, pp. 567-568 is illustrated in FIG. 1. The machine includes an aluminium plate which supports two glass plates. The distance between the glass plates is manually adjustable using 4 control knobs and is set to form a downward-pointing wedge-shaped space such that when aquatic insect culture is poured between the plates the larger specimens are captured higher up the plates and the smaller specimens are captured lower down the plates. However, in an experiment it was estimated that for *An. albimanus* the sorting efficiency of this machine was about 85% which meant that 15% of females were present after sorting. This is not sufficient efficiency to be of use in sterile insect techniques. In addition, use of the instrument is relatively labour-intensive as the spacing needs to be adjusted in use and therefore re-adjusted for each new batch of specimens to be sorted.

Another device is illustrated in FIG. 2 and is described by Evans F. D. S. and Evans H. T. in "A simple separator for mosquito larvae and pupae" in Mosquito News 28(4); 649-650. The device has three tubes, two placed in a horizontal plane with each other and being fixed. The third tube is placed underneath the two tubes and is moveable to provide an adjustable gap for sorting larvae from pupae.

In order to sort a sample the sample is poured between the two cylinders so that it flows over the third cylinder. Whilst the larger pupae are caught in the gap between the upper two cylinders and the lower third cylinder, the smaller larvae pass through the gap and can be collected. However, as the pupae get caught between the cylinders they impede the passage of the larvae and therefore the device cannot be used for high throughput sorting.

Cold water separation is a technique for separating larvae from pupae. In cold water separation larvae and pupae are immobilised in cold water (3-4° C.). At this temperature pupae float in water and larvae sink so the pupae and larvae automatically separate. The pupae can then be separated from the larvae, for example, by decanting or use of a vacuum picker. In experiments cold water separation has been found to cause damage and cold shock to the pupae. Additionally, the technique can only sort to around 80-90% efficiency meaning that the remaining larvae have to be sorted by hand. Furthermore, its efficiency is dependent upon the species of mosquito to be sorted.

Finally, the McCray sorter illustrated in FIG. 3 was developed to sort larvae from pupae. The sorter includes a plurality of slots present in a chamber. Larvae and pupae are poured into the device and a stream of water washes the larvae and pupae onto the slots. The larger female pupae are trapped by the slots but the male pupae and larvae wash through the slots and in this way the female pupae are separated from the male pupae and larvae. However, as with the device described by Evans and Evans the pupae trapped by the slots prevent impede the passage of larvae through the slots meaning the McCray sorter is not suitable for high throughput sorting as the pupae have to be removed from the slots periodically. Additionally, there is no method for removing the larvae from the male pupae.

There is, therefore, no device which appears to efficiently sort larvae from pupae and male pupae from female pupae.

SUMMARY

In accordance with an aspect of the present invention there is provided an apparatus to sort arthropod larvae and/or pupae comprising a first and second bar and two parallel bars, each of the parallel bars having a first pivotal attachment to the first bar and a second pivotal attachment to the second bar, such that rotating the parallel bars relative to the first bar changes the distance between adjacent parallel bars. The apparatus is particularly suited to sorting insect larvae and/or pupae and even more particularly suited to sorting mosquito larvae and pupae. Thus, it is preferred that the arthropod is an insect, more preferably Diptera, and particularly mosquitoes such as *Anopheles* (especially *Anopheles gambiae*) and/or *Aedes* (especially *Aedes aegypti*) species.

The apparatus may have a closed frame having two pairs of opposing sides, one pair of opposing sides being formed by the parallel bars and the second pair of opposing sides being formed by the first bar and the second bar, each one of the bars being pivotally attached to each of the bars forming the other pair of opposing sides.

Optionally there may be a third parallel bar having a first pivotal attachment to the first bar and a second pivotal attachment to the second bar. In an alternative arrangement there is provided a third parallel bar and third and fourth bars, the third and fourth bars having a pivotal attachment to both of the third parallel bar and one of the two parallel bars.

The first and second bars each comprise at least two hingable portions, the first hingable portion having a pivotal attachment to the one of the parallel bars and a pivotal attachment to another hingable portion, and the second hingable portion having a pivotal attachment to the other one of the parallel bars and a pivotal attachment to another hingable portion.

The apparatus may be provided with one or more bars in between and parallel to the first and second bars to form a mesh.

The apparatus preferably includes an element configured to maintain and/or adjust an angle between the first bars and the plurality of parallel bars or distance between the plurality of parallel bars. This element allows the distance between the plurality of bars to be easily changed so that it is optimised for sorting different types of pupae and/or larvae according to their size.

The element may be a threaded screw and the sorting apparatus provided with two fasteners having threaded portions complementary to the threaded screw. The two fasteners may be mounted on the first bar and the second bar respectively.

Preferably, the distance between adjacent parallel bars is 0-1.0 mm, 0-1.1 mm, 0-1.2 mm, 0-1.3 mm, 0-1.4 mm or 0-1.5 mm, when the angle between a parallel bar and the first bar is ninety degrees. It is also preferred that the distance between adjacent parallel bars is 0-1.1 mm when the angle between a parallel bar and the first bar is ninety degrees. Even more preferably the distance between adjacent parallel bars is 0.5-2.0 mm, 0.5-3.0 mm, 0.7-2.0 mm, 0.7-3.0 mm and most preferably 0.7-1.1 mm, when the angle between a parallel bar and the first bar is ninety degrees.

The bars may be made from one or more of wire (including metal wire, nylon wire or plastic wire); metal bars; plastic bars; and wood bars. The bars may have any suitable cross-section including rectangular, circular, semi-circular, triangular or a rectangular with bevelled corners cross-section.

In accordance with a second aspect of the present invention there is provided an apparatus to sort larvae from pupae comprising a chamber to receive pupae and larvae, the chamber comprising a base and a wall wherein the base comprises at least part of the apparatus of the first aspect of the present invention.

In accordance with a third aspect of the present invention there is provided an apparatus to sex pupae comprising a chamber to receive pupae, the chamber comprising a wall, and a top wherein the top comprises at least part of the apparatus of the first aspect of the present invention.

The chamber of the second or third aspects of the present invention may be removeably attachable to the apparatus the first aspect of the present invention.

In accordance with a fourth aspect of the present invention there is provided a method of sorting arthropod larvae and pupae comprising the steps of: inserting the apparatus as claimed in any one of claims 1 to 14 into water; and placing arthropod larvae and pupae to be sorted above the apparatus.

The method may include the further step of raising and lowering the apparatus. This movement of the apparatus promotes passage of the larvae or pupae through the apparatus.

In accordance with a fifth aspect of the present invention there is provided a method of sorting pupae according to size, comprising inserting the apparatus of the first, second or third aspects of the present invention into water including pupae to be sorted such that pupae of a certain size are moved from the surface of the water. One size of pupae is therefore separated from another. This may be within an all male, all female or mixed population.

In accordance with a sixth aspect of the present invention there is provided a method of sexing pupae comprising inserting the apparatus of the first, second or third aspects of the present invention into water including pupae to be sexed such that the pupae are moved from the surface of the water. One sex of pupae is therefore separated from another, i.e. males from females.

Under some circumstance, the method may include raising and lowering steps, for instance as described above, but this is generally not preferred for sexing.

The arthropod may be an insect, such as a Dipteran. It may be a mosquito such as *Anopheles* (especially *Anopheles gambiae*) and/or *Aedes* (especially *Aedes aegypti*) species.

DESCRIPTION

Figure 1:
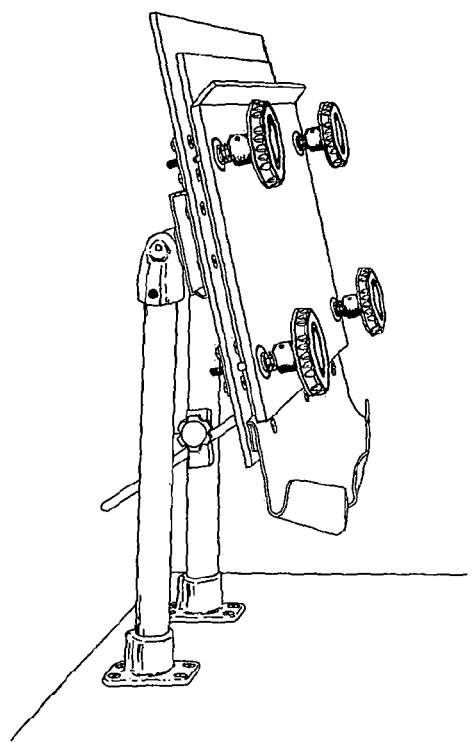
FIGS. 1 to 3 illustrate known apparatus for sorting insects.
Figure 2:
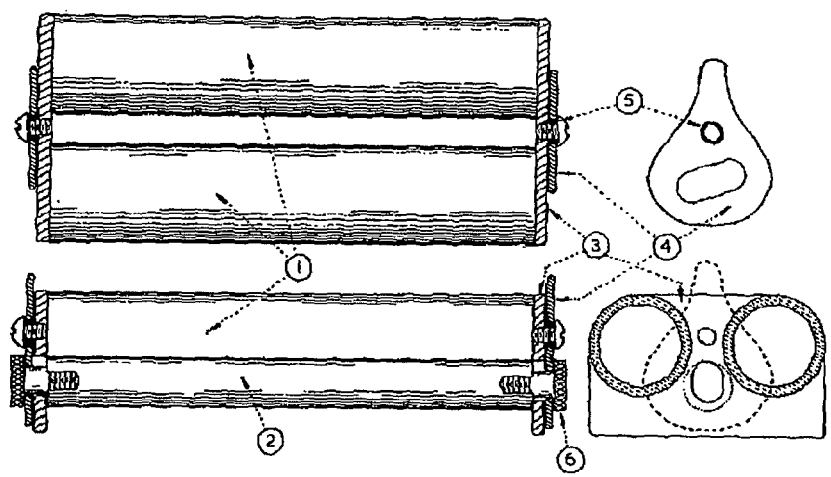
Figure 3:
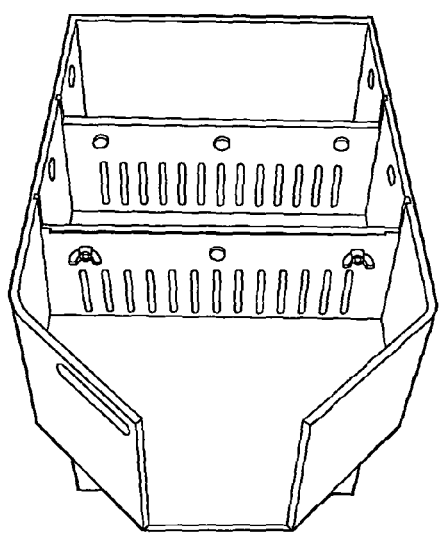
Figure 4:
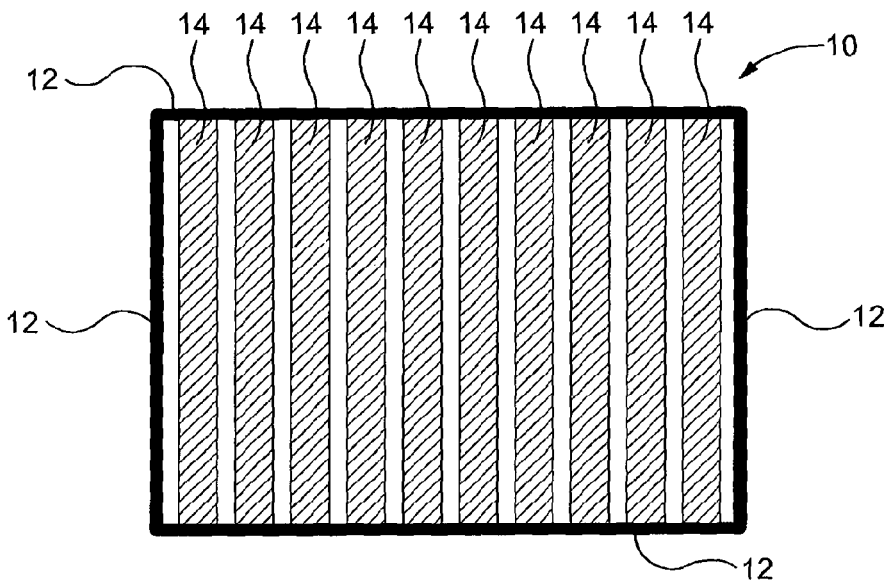
FIG. 4 is a bird's eye view of sorting apparatus in accordance with the present invention.

The sorting apparatus 10 of the present invention in one embodiment comprises a frame formed by four bars 12 as illustrated in FIG. 4. Each bar 12 is rotatably connected at each end to another one of the bars 12 so that the frame forms a quadrilateral shape with two pairs of parallel sides. As the bars 12 are rotatably connected to each other the frame may have its shape altered so that the angle at the corner of the frame changes whilst the bars forming opposing sides of the frame remain parallel.

The sorting apparatus 10 is also provided with a number of intermediate bars 14 extending from one side of the frame to the opposing side of the frame. Each intermediate bar 14 is separated from its adjacent bars by a gap, preferably of 1.1 mm, when the angle at the frame's corners is 90°. Each of the intermediate bars 14 is rotatably connected to the bars 12 forming the frame.

Figure 5:
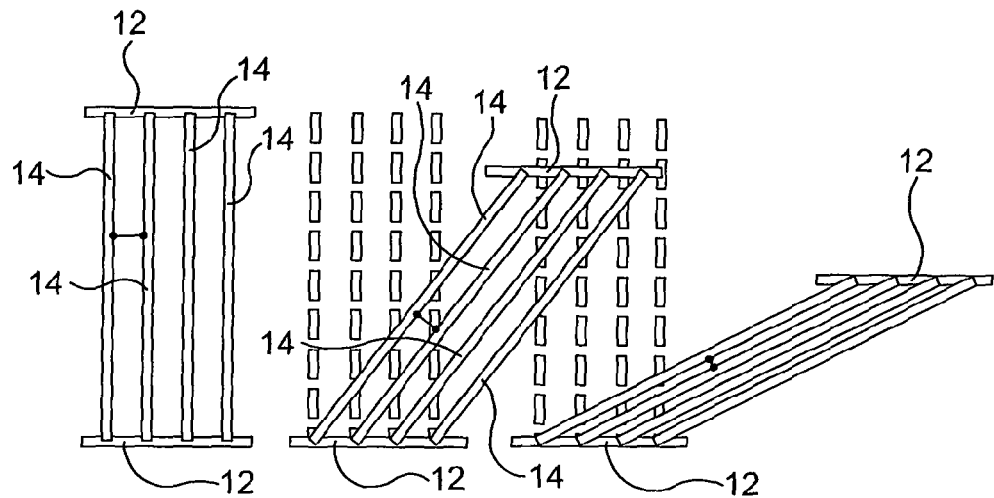
FIG. 5 illustrates different configurations of the sorting apparatus of FIG. 4.

By rotatably connecting the bars of the frame and the intermediate bars the angle at the intersection of the bars of the frame may be adjusted by a user. FIG. 5 shows how, as the angle between connected bars becomes further from 90°, the distance between adjacent bars decreases (the original position of the bars is shown by the dotted lines). This provides the advantage that the distance between adjacent bars can be calculated by the angle at a connection between bars. Alternatively, the distance between adjacent bars may be measured using any suitable means.

Figure 6:
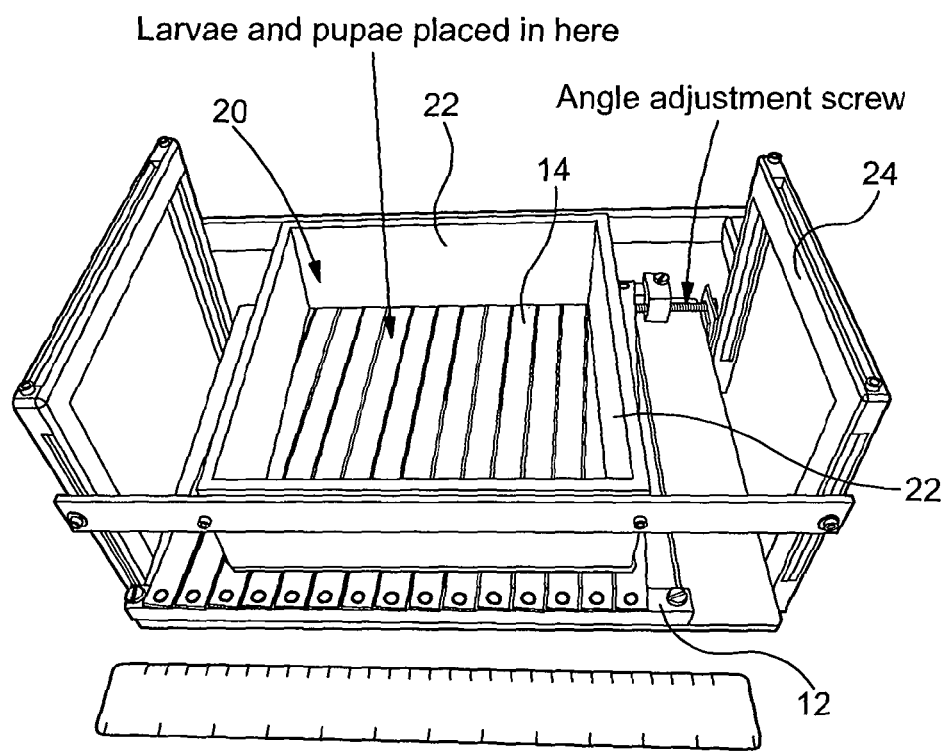
FIG. 6 illustrates sorting apparatus including a chamber for sorting larvae and pupae.
Figure 8:
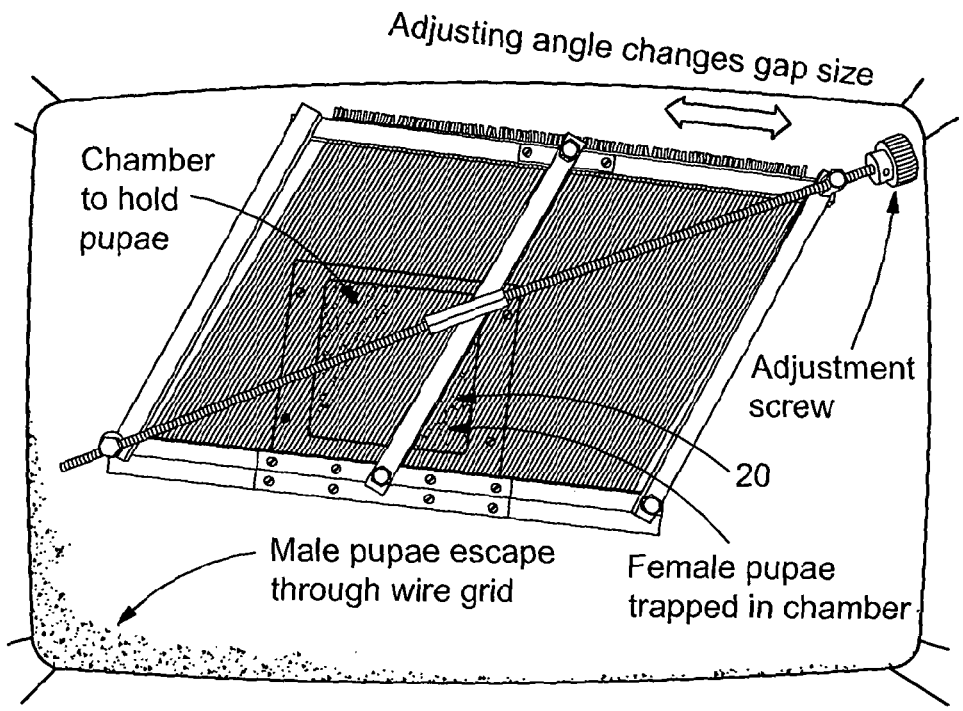
FIG. 8 illustrates sorting apparatus including a chamber for sorting pupae of different sexes.

The sorting apparatus 10 is preferably provided with a chamber 20. The chamber comprises four walls 22 which connect to form an enclosure to receive a sample containing larvae and pupae to be sorted. Another side of the chamber is at least partially formed by the intermediate bars 14 and/or the bars of the frame 12. The chamber may have one open side as illustrated in FIG. 6 or be enclosed with a further wall being provided on the remaining side as illustrated in FIG. 8. Examples of chambers 20 are illustrated in FIGS. 6 and 8.

The sorting apparatus 10 may additionally be provided with suitable means to alter and/or maintain the angle between intersecting bars. For example, clips may be attached to the frame to hold the angle between intersecting bars.

Alternatively, as illustrated in FIGS. 6 and 8, the frame may be provided with a threaded screw arrangement where a threaded screw is used to alter the angle at the corners of the frame. In FIG. 6 the sorting apparatus is provided with a support structure 24. The support structure comprises four struts forming a fixed rectangle in a plane parallel to the plane of the bars of the sorting apparatus. One bar of the frame is affixed to one of the four struts (or forms one of the four struts). The bar forming the opposing side of the frame is provided with at least one nut configured to receive a threaded screw. Another nut is affixed to a strut so that the threaded screw can pass through both nuts at the same time thereby allowing the bar to be moved relative to the frame by rotating the screw.

By fixing one side of the frame relative to the support structure and allowing the opposing side of the frame to be moveable relative to the support structure by means of a threaded screw the angle and therefore distance between intersecting bars can be readily changed and fixed.

In FIG. 8 the sorting apparatus is provided with two nuts each on diagonally opposed corners of the frame. The threaded screw is then passed through the nuts. Rotating the screw one way will cause the two diagonally situated corners to move closer together thereby altering the angle at the corner of the frame and the distance between the bars of the device. Likewise rotating the screw in the other direction will cause the diagonally situated corners to move apart altering the angle at the corners of the frame.

As will be understood by one skilled in the art the methods of changing and fixing the positions of the bars of the frame are provided by way of example only and any other suitable means may be used. Additionally, any type of fastener may be used to connect a threaded screw to the sorting apparatus and/or a support structure.

Figure 7:
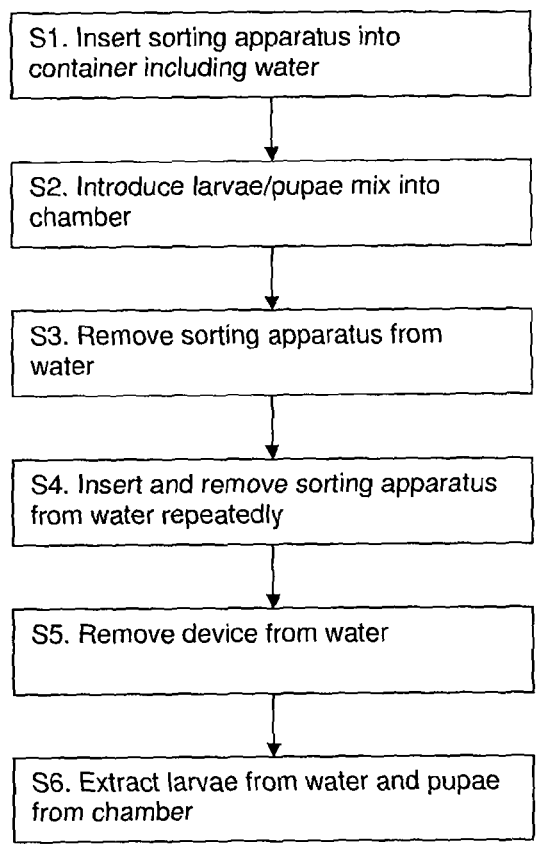
FIG. 7 is a flow diagram of a method of using the sorting apparatus of FIG. 6.

A method of using the sorting apparatus to sort larvae from pupae will now be described with reference to FIGS. 6 and 7. In the first step (S1) the sorting apparatus 10, including the chamber 20 is placed in a large container (not shown) with sufficient water to approximately half fill the chamber 20 illustrated in FIG. 6. Larvae and pupae to be sorted can then be placed into the chamber 20 (S2) and the sorting apparatus 10 lifted out of the water (S3). As the device is lifted out of the water the smaller larvae pass through the gaps between the bars 12, 14 of the sorting apparatus into the container 24. The larger pupae cannot pass through the bars and therefore remain in the chamber 20. As the pupae will block the passage of some larvae through the bars the sorting apparatus 10 it is advantageous to repeatedly inserted and remove the sorting apparatus from the water (S3). Inserting the sorting apparatus from the water serves to dislodge any pupae from the gaps between bars thereby enabling further larvae to pass through the gaps when the sorting apparatus is lifted from the water again. This allows a high percentage of the larvae to pass through gaps between the bars. We have shown that lifting the sorting apparatus in and out of the water in the container about 10 times sorts about 99% of the larvae from the pupae.

Once the sorting apparatus has been inserted into the water a sufficient number of times the sorting apparatus can be removed from the water (S5) and the larvae can be removed from the water in the container 24 and the pupae can be removed from the chamber.

Figure 9:
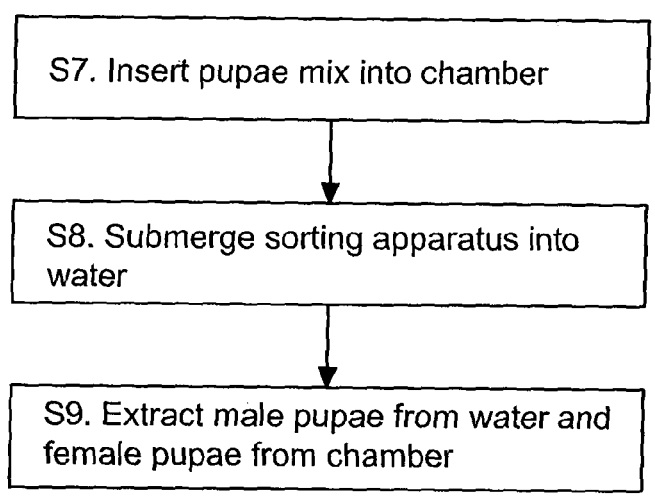
FIG. 9 is a flow diagram of a method of using the sorting apparatus of FIG. 8.

A method of sorting male and female pupae will now be described with reference to FIG. 9. This method makes use of the pupae's instinct to swim towards the surface of water. In contrast to the embodiment described above the chamber must be completely enclosed with a base, walls and one side being formed by the bars of the sorting apparatus as illustrated in FIG. 8. In use, the apparatus is orientated so that the chamber 20 enters the water in a container before the bars of the apparatus does.

In this method the male and female pupae to be sorted are placed within the chamber 20 (S7) and the apparatus is placed in a container 26 of water with the bars uppermost so that it is entirely submerged (S8).

As discussed above pupae have an instinct to swim to the surface of the water. This means that the pupae within the chamber swim upwards towards the bars 12, 14 of the sorting apparatus 10. The male pupae are smaller than the female pupae and can pass through the gaps between the bars whereas the female pupae cannot pass through the gaps between the bars 12, 14 and remain within the chamber 20.

Male pupae can then be collected from the surface of the water and the female pupae can be removed from the chamber (S.9).

It is estimated that a device with a frame size of 10×10 cm can sort 100000 pupae in an hour. The efficiency of sorting was tested by sorting over 3 million male pupae and resulted in an average contamination of 0.03%, contamination here meaning the proportion of female pupae found in the 'male' pupae collection after sorting.

As will be understood by the skilled person the bars of the apparatus may be made from any suitable material such as nylon wire, plastic wire, metal wire, wood, plastic, metal. Additionally the bars may have any suitable cross-section. For example, the bars may have a rectangular, circular, semi-circular, triangular or a rectangular with bevelled corners cross-section. The bars may have any suitable dimension.

An example of the use of wire in a pupae separation device is provided in a publication from 1972 by Sharma et al ("A device for the rapid separation of male and female mosquito pupae"; V. P. Sharma, R. S. Patterson, and H. R. Ford; Bull World Health Organ. 1972; 47(3): 429-432). It uses nylon wire and is designed for separating pupae of *C. p. fatigans*, but is not adjustable and therefore impractical unless set up very precisely for each species. An additional problem with fixed wire spacing is that caused by batch-to-batch size variation within a species, i.e. variation in size from one tray or time to another due to variation in environment (food, temperature etc) or, potentially, genetics, meaning that adjustment may be required between some batches (even from the same species).

Additionally, further sets of intermediate bars may be provided between one or more pairs of the frame. For example, as illustrated in FIG. 8 a first set of parallel bars are parallel to one pair of opposing sides and the other set of parallel bars are parallel to the other pair of opposing sides.

The bars forming the frame and/or parallel bars need not be linear as illustrated in the Figures but may have any suitable shape. For example, where there is only one set of parallel bars the sides of the frame not parallel to the bars may have a curved shape. Alternatively, a set of parallel bars may have any suitable shape provided that the bars are parallel.

The skilled person will understand that features of the two embodiments are readily interchangeable. For example, the adjustment screw described with reference to FIG. 6 may equally be applied to the sorting apparatus of FIG. 8 and vice versa. Likewise the sorting apparatus of FIG. 6 may be provided with the further sets of parallel bars illustrated in FIG. 8 and the sorting apparatus of FIG. 8 may be provided only with intermediate bars running parallel to one set of opposing sides.

Additionally, the chamber is not necessary for implementing the sorting methods described with reference to FIGS. 4 and 6. For example, if the sides of the container for liquid receive the frame of the sorting apparatus with a distance less than or equal to that between the intermediate bars between the sides of the frame and the container the sorting apparatus may be used without the chamber.

The distance between adjacent intermediate bars or the intermediate bars and the frame may be any suitable distance. An optimal range of distance between the bars may be determined by the arthropod to be sorted. The size of pupaelarvae will differ between various arthropods. For most arthropods, the preferable distance between the bars is 0-3 mm. More preferably, the distance is 0-2.5 mm, 0-2 mm or 0-1.5 mm.

The arthropod may be an insect, such as a Dipteran. It may be a mosquito such as *Anopheles* (especially *Anopheles gambiae*) and/or *Aedes* (especially *Aedes aegypti*) species. Taking mosquitoes as an example, the distance is preferably 0-1.1 mm. Even more preferably the spacing is 0.7-1.1 mm. Other preferred ranges are mentioned above.

The sorting apparatus may be provided with one or more handles or any other suitable means to facilitate the repeated insertion and removal from the water. Alternatively, the sorting apparatus may be connected to means such as a motor to automatically insert and remove the apparatus from the water.

Figure 10:
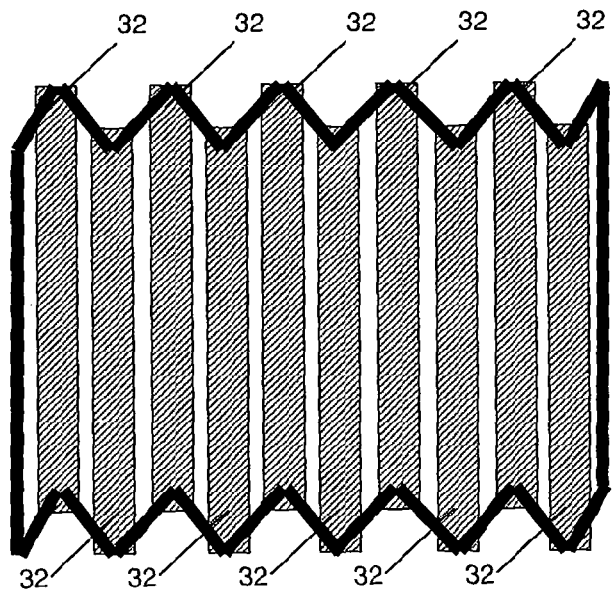
FIG. 10 illustrates a sorting apparatus with bars forming a frame which are rotatably connected at either end to adjacent parallel bars enabling the frame to be compressed and elongated.
Figure 11:
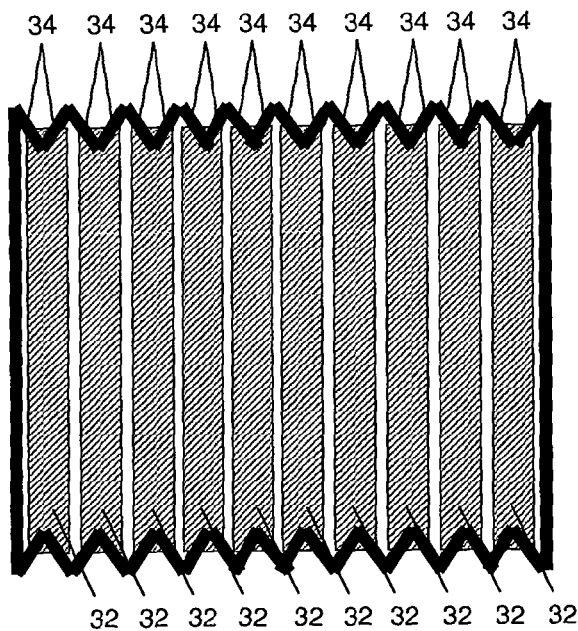
FIG. 11 illustrates a sorting apparatus with bars forming a frame such that adjacent parallel bars are connected via two bars.

Further alternative embodiments of the sorting apparatus are illustrated in FIGS. 10 and 11. In these Figures the frame comprises a set of parallel bars 32 as described above. In FIG. 10 bars forming a frame are rotatably connected at either end to adjacent parallel bars enabling the frame to be compressed and elongated by rotating the bars forming the frame relative to the parallel bars. In FIG. 11 the bars forming a frame are rotatably connected at one end to one of the parallel bars and at the other end to another of the bars forming a frame such that adjacent parallel bars are connected via two bars. This configuration enables a concertina motion to vary the distance between the parallel bars of the frame. The distance between the bars may be adjusted using a threaded screw connected along the distance of an edge formed by the hinged portions 34 or any other suitable means.

In one preferred embodiment, there is provided apparatus for sorting insect larvae from pupae and for sexing pupae on the basis of size (which sorts different sexes), especially in mosquitoes. The apparatus comprises two parallel bars pivotally mounted in a frame such that the distance between the bars is adjustable by angling the frame. Insect larvae and pupae may be inserted into a chamber with one side formed by the grid of bars and inserted into water to separate the different forms. The pupae may then be inserted into a chamber covered by a grid of bars and submerged in water. The smaller pupae can swim through the bars and the larger pupae remain trapped. In mosquitoes the smaller pupae tend to be males and the larger pupae females.

ADDITIONAL REFERENCES

Focks, D. (1980). "An improved separator for the developmental stages, sexes, and species of mosquitoes (Diptera: Culicidae)." *J Med Entomol*, 17, pp. 567-568

Bar-Zeev M. and Galun R. (1961) A magnetic method of separating mosquito pupae from larvae. 1961. MOSQ. NEWS 21(3): 225-28

Evans F. D. S. and Evans H. T. 1968 A simple separator for mosquito larvae and pupae. Mosq news, 28(4); 649-650

Fay R. W., Mccray, E. M. R. and Kilpatrick W. (1963) Mass production of sterilized male *Aedes aegypti*. 1963. MOSQ. NEWS 23(3): 210-14

Fay R W, Morlan H B (1959) A mechanical device for separating the developmental stages, sexes, and species of mosquitoes. Mosq News 19 144-147.

Focks, D. A. (1980) An improved separator for the developmental stages, sexes, and species of mosquitoes (diptera: culicidae) *Journal of Medical Entomology Vol.* 17, no. 6: 567-568

Hazard E I (1967) Modification of the ice water method for harvesting *Anopheles* and Culex pupae. Mosq News 27 115-116

Lin C S, Georghiou G P (1976) Tolerance of mosquito larvae and pupae to carbon dioxide anesthesia. Mosq News 36:460-461

M. A. Ansari, K. R. P. Singh, G. D. Brooks and P. R. Malhotra. (1977) A device for separation of pupae from larvae of *Aedes aegypti* (diptera: culicidae). J. MED. ENTOMOL. 14(2): 241-43

M. A. Ansari, K. R. P. Singh, G. D. Brooks, P. R. Malhotra and V. Vaidyanathan. (1975) The developent of procedures for mass rearing of *Aedes aegypti* (I). WHO/VBC/75.560:9P.

McCray E M (1961) A mechanical device for the rapid sexing of *Aedes aegypti* pupae. J Econ Entomol 54 p 819

Ramakrishnan S. P., Krishnamurthy B. S. and Singfa M. N. (1963) A simple technique for rapid separation of mosquito pupae by sudden chilling. 1963. Indian J. Malarlol, 17(2/3): 119-21

Vartak P. H. Ramachandran R. Mukherjee S. N. (1989) A device for separating mosquito larvae and pupae. J. COMMUN. DIS. 21(2): 148-52.

Sharma V. P., Patterson, R. S. and Ford H. R. A device for the rapid separation of males and female pupae. Bulletin World Health Organ: 47(3): 429-432 (1972).

Weathersby A. B. (1063) Harvesting mosquito pupae with cold water. 1963. MOSQ. NEWS 23(3): 249-51.

Weathersby A B (1963) Harvesting mosquito pupae with cold water. Mosq News L1-2927pdf 23:249-251

The invention claimed is:

1. An apparatus to sort arthropod larvae and/or pupae comprising:

a first and second bar and two parallel bars, each of the parallel bars having a first pivotal attachment to said first bar and a second pivotal attachment to said second bar, such that rotating said parallel bars relative to said first bar changes the distance between adjacent parallel bars, wherein said apparatus further comprises an element configured to maintain and/or adjust distance between said plurality of parallel bars, wherein said element comprises a threaded screw and said apparatus is provided with two fasteners having threaded portions complementary to said threaded screw, said two fasteners being mounted on said first bar and said second bar respectively.

2. The apparatus of claim 1, wherein said apparatus further comprises a closed frame comprising two pairs of opposing sides, one pair of opposing sides being formed by said parallel bars and the second pair of opposing sides being formed by said first bar and said second bar, each one of the bars of said one pair of opposing sides being pivotally attached to each of the bars forming said second pair of opposing sides.

3. The apparatus of claim 1, further comprising a third parallel bar, said third parallel bar having a first pivotal attachment to said first bar and a second pivotal attachment to said second bar.

4. The apparatus of claim 1, further comprising a third parallel bar and third and fourth bars, said third and fourth bars having a pivotal attachment to both of said third parallel bar and one of said two parallel bars.

5. The apparatus of claim 1, wherein said first and second bars each comprise at least two hingable portions,
the first hingable portion having a pivotal attachment to the one of said parallel bars and a pivotal attachment to another hingable portion, and
the second hingable portion having a pivotal attachment to the other one of said parallel bars and a pivotal attachment to another hingable portion.

6. The apparatus of claim 1, further comprising one or more bars in between and parallel to said first and second bars.

7. The apparatus of claim 1, wherein the distance between adjacent parallel bars is 0-1.1 mm when the angle between a parallel bar and said first bar is ninety degrees.

8. The apparatus of claim 1, wherein the distance between adjacent parallel bars is 0.7-1.1 mm when the angle between a parallel bar and said first bar is ninety degrees.

9. The apparatus of claim 1 wherein said bars are made from one or more of wire, metal bars, plastic bars, or wood bars.

10. The apparatus of claim 1 wherein said bars have a rectangular, circular, semi-circular, triangular or a rectangular with bevelled corners cross-section.

11. The apparatus of claim 1, further comprising a chamber to receive pupae and larvae, said chamber comprising a base and a wall.

12. The apparatus of claim 1, further comprising a chamber to receive pupae, said chamber comprising a base, a wall, and a top.

13. The apparatus of claim 11 wherein said chamber is removeably attachable to said apparatus.

14. A method of sorting arthropod larvae and pupae comprising the steps of:
a) providing said apparatus of claim 1;
b) inserting said apparatus of claim 1 into water; and
c) placing arthropod larvae and pupae to be sorted above said apparatus.

15. The method of claim 14, further comprising the step of:
d) raising and lowering said apparatus such that larvae pass through the apparatus.

16. A method of sorting pupae according to size, comprising the steps of:
a) providing said apparatus of claim 1;
b) inserting said apparatus of claim 1 into water including pupae to be size-sorted such that the pupae are moved from the surface of the water; and
c) raising and lowering said apparatus such that pupae of a certain size pass through the apparatus.

17. A method of sexing pupae comprising providing said apparatus of claim 1, inserting said apparatus of claim 1 into water including pupae to be sexed such that the pupae are moved from the surface of the water.

* * * * *